(12) United States Patent
Engstrom

(10) Patent No.: US 9,427,359 B1
(45) Date of Patent: Aug. 30, 2016

(54) ADJUSTABLE EYELID COVER DEVICE AND METHOD

(71) Applicant: Mark C. Engstrom, Marine on St. Croix, MN (US)

(72) Inventor: Mark C. Engstrom, Marine on St. Croix, MN (US)

(73) Assignee: Mark C Engstrom, Marine On St Croix, MN (US)

( * ) Notice: Subject to any disclaimer, the term of this patent is extended or adjusted under 35 U.S.C. 154(b) by 344 days.

(21) Appl. No.: 14/045,932

(22) Filed: Oct. 4, 2013

(51) Int. Cl.
 A61F 9/00 (2006.01)
 A61F 9/04 (2006.01)

(52) U.S. Cl.
 CPC .................................. A61F 9/045 (2013.01)

(58) Field of Classification Search
 CPC ........... A61F 9/02; A61F 9/045; G02C 1/10; A63B 33/002
 USPC ........ 2/12, 13, 431; 351/103, 110, 124, 149, 351/150, 153, 159.28, 159.75; 446/27; D16/300, 301, 310, 311, 330, 339, 340
 See application file for complete search history.

(56) References Cited

U.S. PATENT DOCUMENTS

| | | | | |
|---|---|---|---|---|
| 235,930 | A * | 12/1880 | Borsch | 351/110 |
| 1,310,077 | A * | 7/1919 | Heaford | G02C 9/00 2/13 |
| 2,095,193 | A * | 10/1937 | Haar | G02C 7/16 2/12 |
| 2,456,334 | A * | 12/1948 | Shindel | G02C 1/04 2/12 |
| 4,391,498 | A * | 7/1983 | Rengstorff | G02C 3/003 351/111 |
| 4,790,031 | A * | 12/1988 | Duerer | A61F 9/02 128/858 |
| 5,313,671 | A * | 5/1994 | Flory | A63B 33/002 2/428 |
| 5,835,182 | A * | 11/1998 | Einarsson | G02C 11/12 2/12 |
| 5,927,281 | A * | 7/1999 | Monteleone | A61F 9/0008 128/858 |
| 6,081,934 | A * | 7/2000 | Stefanovsky et al. | 2/431 |
| 6,290,355 | B1 * | 9/2001 | Chen | G02C 1/04 351/103 |
| 6,543,056 | B2 * | 4/2003 | Spiteri | A61F 9/04 2/15 |
| 6,776,482 | B1 * | 8/2004 | Xiao | G02C 1/02 351/110 |
| 7,883,205 | B2 * | 2/2011 | Begg | 351/48 |
| 2003/0145368 | A1 * | 8/2003 | Johnson | A61F 9/029 2/434 |
| 2004/0016037 | A1 * | 1/2004 | Griesbach, III | A41D 13/1184 2/12 |
| 2006/0010587 | A1 * | 1/2006 | Yokota | A63B 33/002 2/429 |
| 2006/0109418 | A1 * | 5/2006 | Resler | G02C 3/003 351/44 |
| 2008/0143951 | A1 * | 6/2008 | Won | G02C 9/04 351/57 |
| 2008/0170198 | A1 * | 7/2008 | Resler | G02C 3/003 351/44 |
| 2010/0122398 | A1 * | 5/2010 | Luciano | A61F 9/04 2/173 |
| 2012/0005811 | A1 * | 1/2012 | McCrory | A61F 9/029 2/439 |
| 2012/0311773 | A1 * | 12/2012 | Anderson | A63B 33/002 2/431 |
| 2013/0070195 | A1 * | 3/2013 | Workman | G02C 7/086 351/47 |
| 2013/0194538 | A1 * | 8/2013 | Junkins | G02C 9/04 351/47 |
| 2013/0276216 | A1 * | 10/2013 | Grad | A61F 9/025 2/431 |
| 2015/0042945 | A1 * | 2/2015 | Curley | G02C 9/00 351/57 |
| 2015/0194067 | A1 * | 7/2015 | Kindschuh | G09B 19/0023 434/365 |

* cited by examiner

Primary Examiner — Khaled Annis

(57) ABSTRACT

An adjustable eyelid cover device and method for protecting a user's eyelids from being sunburned. The adjustable eyelid cover device and method includes an eyelid cover assembly including a pair of eyelid cover members being adapted to fit over a user's eyelids when a user has one's eyes closed; an elastic band adjustably interconnecting the eyelid cover members and being adapted to fasten about a user's head to position the eyelid cover members over the user's eyelids; and a size adjustment member engagable to at least a portion of the elastic band to adjust a size of the elastic band about the user's head.

3 Claims, 4 Drawing Sheets

ADJUSTABLE EYELID COVER DEVICE AND METHOD

BACKGROUND OF THE INVENTION

Field of the Invention

The present invention relates to eyelid sun blockers and more particularly pertains to a new adjustable eyelid cover device and method for protecting a user's eyelids from being sunburned.

Description of the Prior Art

The use of eyelid sun blockers is known in the prior art. More specifically, eyelid sun blockers heretofore devised and utilized are known to consist basically of familiar, expected and obvious structural configurations, notwithstanding the myriad of designs encompassed by the crowded prior art which have been developed for the fulfillment of countless objectives and requirements.

The prior art includes a therapeutic eye and eyelid cover which includes heating means and means for saturating the air enclosed against the face with water vapor, preventing evaporation from the eye and eye lids and enhancing heat transfer to the covered tissue. Another prior art includes a flexible eyelid cover pre-formed for secure placement in an eye socket over the eyelid with only a single wetting and without the use of adhesive. The cover is formed of closed cell thermoplastic UV barrier material having a plurality of suction-cup like dimples disposed on the rear surface thereof and which upon initial wetting, conforms to the shape of the eyelid and adheres thereto. Also another prior art includes an eye shield including a U-shaped bridge and shield members connected to the U-shaped bridge. Yet, another prior art describes a flexible eyelid cover includes an adhesive having a decorative design arranged opposite an inner surface of the flexible eyelid cover. Further, another prior art describes an eye shade including a first side connected to an intermediate layer. A second side is connected to the intermediate layer. A first outer eye portion and a second outer eye portion are formed from the first side, the intermediate layer and the second side. The first and second outer eye portions extend outward. The first outer eye portion and the second outer eye portion are convex shaped.

While these devices fulfill their respective, particular objectives and requirements, the aforementioned patents do not disclose a new adjustable eyelid cover device and method.

SUMMARY OF THE INVENTION

The general purpose of the present invention, which will be described subsequently in greater detail, is to provide a new adjustable eyelid cover device and method which has many of the advantages of the eyelid sun blockers mentioned heretofore and many novel features that result in a new adjustable eyelid cover device and method which is not anticipated, rendered obvious, suggested, or even implied by any of the prior art eyelid sun blockers, either alone or in any combination thereof. The present invention includes an eyelid cover assembly including a pair of eyelid cover members being adapted to fit over a user's eyelids when a user has one's eyes closed; an elastic band adjustably interconnecting the eyelid cover members and being adapted to fasten about a user's head to position the eyelid cover members over the user's eyelids; and a size adjustment member engagable to at least a portion of the elastic band to adjust a size of the elastic band about the user's head. None of the prior art includes the combination of the elements of the present invention.

There has thus been outlined, rather broadly, the more important features of the adjustable eyelid cover device and method in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new adjustable eyelid cover device and method which has many of the advantages of the eyelid sun blockers mentioned heretofore and many novel features that result in a new adjustable eyelid cover device and method which is not anticipated, rendered obvious, suggested, or even implied by any of the prior art eyelid sun blockers, either alone or in any combination thereof.

Still another object of the present invention is to provide a new adjustable eyelid cover device and method for protecting a user's eyelids from being sunburned.

Still yet another object of the present invention is to provide a new adjustable eyelid cover device and method that can be comfortably secured about a user's head without hindrance and without causing tan lines while the user is lying down.

Even still another object of the present invention is to provide a new adjustable eyelid cover device and method where one size fits all with the eyelid cover members being adjustable along the elastic headband.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Figure 1:
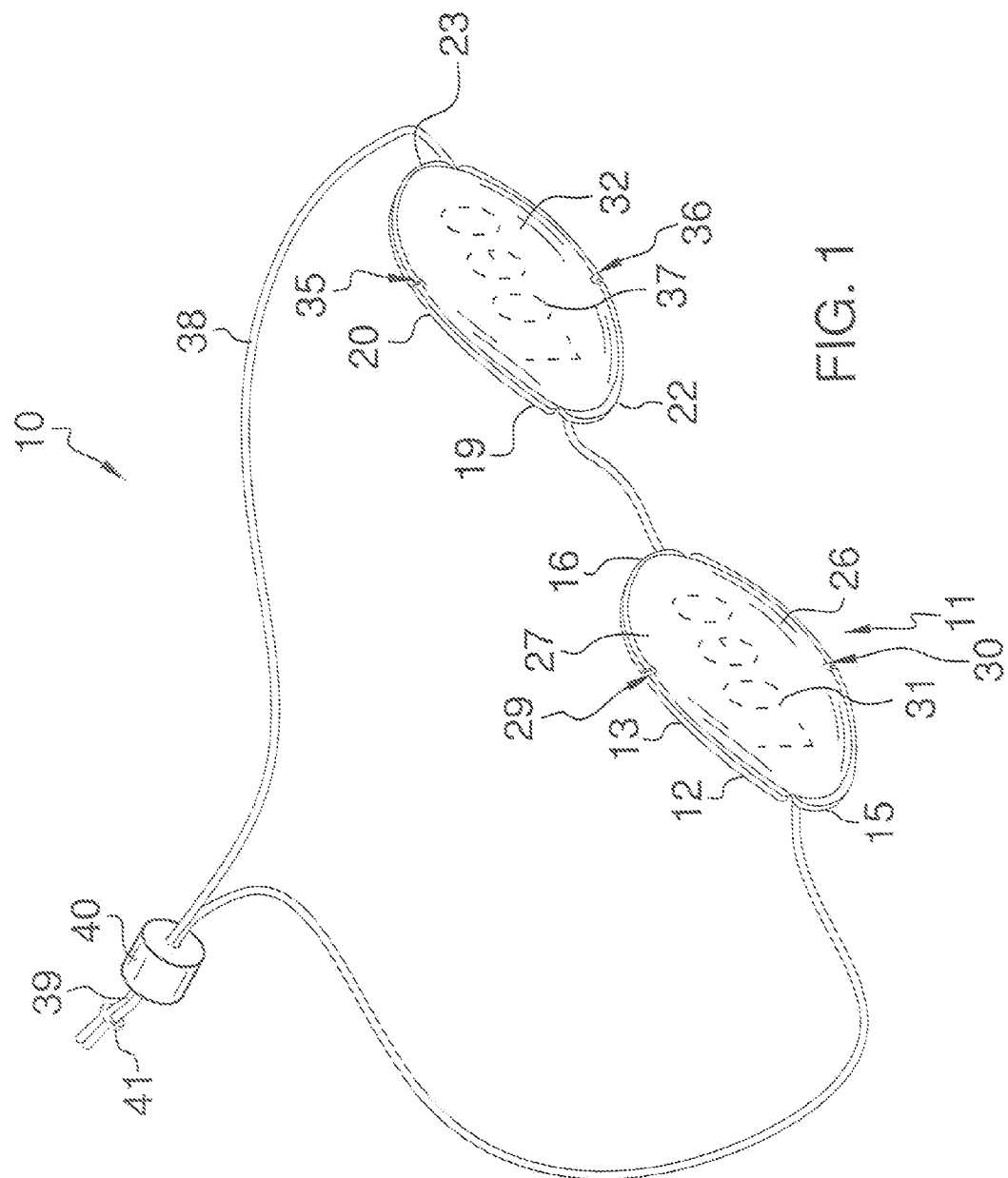
FIG. 1 is a front perspective view of a new adjustable eyelid cover device and method according to the present invention.

With reference now to the drawings, and in particular to FIGS. 1 through 4 thereof, a new adjustable eyelid cover device and method embodying the principles and concepts of the present invention and generally designated by the reference numeral 10 will be described.

Figure 2:
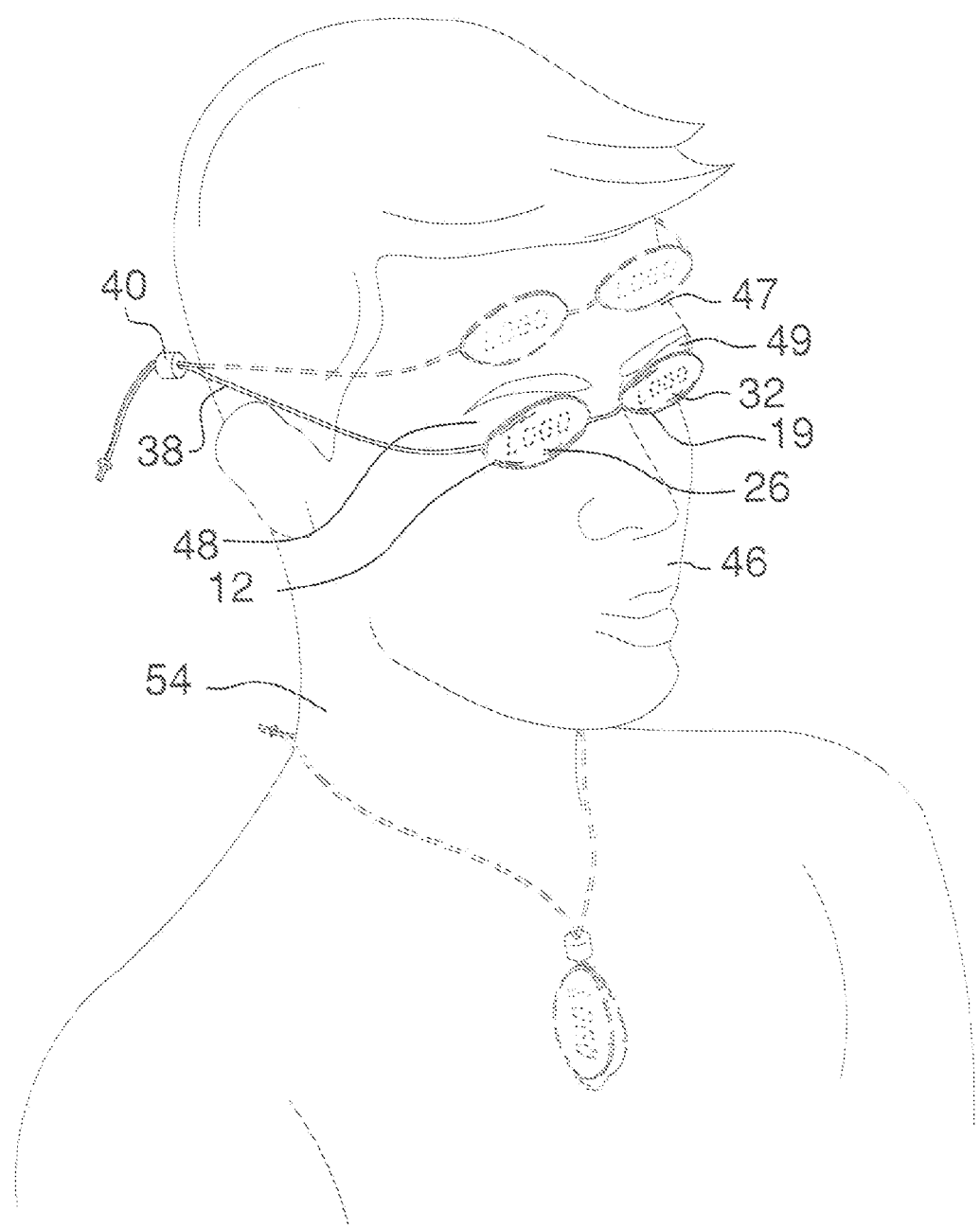
FIG. 2 is a perspective view of the present invention fastened about the head of a user.
Figure 3:
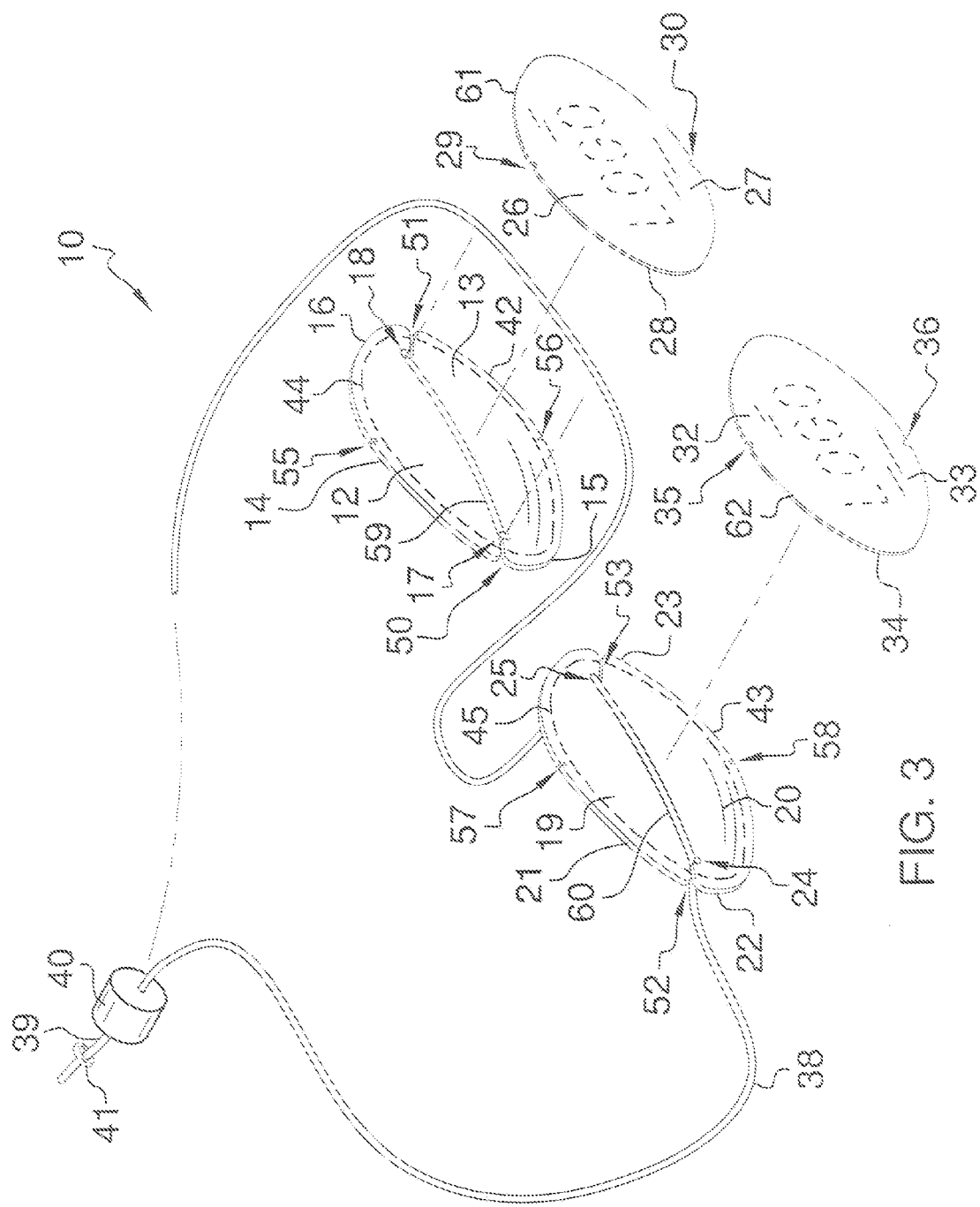
FIG. 3 is an exploded front perspective view of the eyelid cover members of the present invention.

As best illustrated in FIGS. 1 through 3, the adjustable eyelid cover device and method 10 generally comprises an eyelid cover assembly 11 including a pair of eyelid cover members 12,19 being adapted to fit over a user's eyelids 48,49 when a user has one's eyes closed, and also comprises an elastic band 38 adjustably interconnecting the eyelid cover members 12,19 and being adapted to fasten about a user's head 46 to position the eyelid cover members 12,19 over the user's eyelids 48,49 and further comprises a size adjustment member 40 engagable to a portion 39 of the elastic band 38 to adjust a size of the elastic band 38 about the user's head 46.

As illustrated in FIGS. 1-3, each of the eyelid cover members 12,19 may be a thin, semi-flexible piece of material having a generally elliptical shape and having a pair of opposed holes 17,18,24,25 disposed laterally therethrough and passing through a main axis of the respective eyelid over member 12,19 with each hole 17,18,24,25 disposed adjacent to a respective vertex 15,16,22,23 of the piece of material. Each of the eyelid cover members 12,19 may also have a pair of slots 50-53 each extending from the respective hole 17,18,24,25 and disposed through an edge 42,43 of the respective eyelid cover member 12,19 at the respective vertex 15,16,22,23. Further, each of the eyelid cover members 12,19 may be longitudinally curved and may have a convex outer surface 13,20 which faces away from the user's eyelid 48,49 when worn and also may have a concave inner surface 14,21 which faces the user's eyelid 48,49 when worn. In addition, each of the eyelid cover members 12,19 may also have a groove 59,60 disposed in the convex outer surface 13,20 and interconnecting the opposed holes 17,18, 24,25. Each of the eyelid cover members 12,19 may further have a pair of opposed notches 55-58 disposed in the edge 42,43 and passing through a minor axis of the respective eyelid cover member 12,19. Each of the eyelid cover members 12,19 may be made of a substance selected from a group consisting of polyvinyl chloride, polycarbonate, polypropylene and a green flexible material. Each of the eyelid cover members 12,19 may have a length of approximately 2⅜ inches as measured along the main axis of the eyelid cover member 12,19 and may have a width of approximately 1¼ inches as measured along a minor axis of the eyelid cover member 12,19. Also, each of the eyelid cover members 12,19 may have a thickness of approximately 0.04 inches As shown in FIG. 3, the eyelid cover assembly 11 may also include a pair of labels 26,32 each being a flexible piece of material and having an elliptical shape and also having dimensions substantially equivalent to that of the eyelid cover members 12,19. Each of the labels 26,32 may have an inner surface 28,34 which is adhered with adhesive to the convex outer surface 13,20 of the respective eyelid cover member 12,19. Also, each of the labels 26,32 has opposed notches 29,30,35,36 disposed in an edge 61,62 and passing through a minor axis of the respective label 26,32 and which are aligned with the notches 55-58 of the respective eyelid cover member 12,19 when applying the label 26,32. Each of the labels 26,32 may also have an outer surface 27,33 upon which selected indicia 31,37 is displayed. The indicia 31,37 may include fanciful designs and advertisement materials including logos. In addition to the eyelid cover members 12,19 being worn over the user's eyelids 28,29, the eyelid cover members 12,19 may be worn upon a user's forehead 47 when not being used to protect the user's eyelids 48,49 with the indicia 31,37 being visibly displayed for others to see.

As illustrated in FIGS. 1 & 2, the elastic band 38 may extend through the opposed slots 50-53 and through the opposed holes 17,18,24,25 of each of the eyelid cover members 12,19 to interconnect the eyelid cover members 12,19 and may also be received in the grooves 59,60 of the eyelid cover members 12,19 and is substantially flush with the convex outer surface 13,20 and is engagable to the labels 26,32 to prevent the eyelid cover members 12,19 from spinning upon the elastic band 38. A clasp 41 may be fastened about end portions 39 of the elastic band 38 to form an endless loop. The eyelid cover members may be movably engaged upon the elastic band 38 to adjust the spacing between the eyelid cover members 12,19 to accommodate all users. The elastic band 38 may also be made of transparent material to prevent tan lines upon a user's head 46 when worn. The elastic band 38 may be a thin elastic string.

As shown in FIG. 3, the size adjustment member 40 may be a small block of compressible foam material having a length of less than 1 inch. The portion 39 of the elastic band 38 may be overlaid onto itself and engagably extended through the size adjustment member 40 to adjust the size of the elastic band 38.

As a second embodiment, the eyelid cover assembly 11 may further include edging members 44,45 being conventionally disposed along edges 42,43 of the eyelid cover members 12,19 for insulating purposes. Each of the edging members 44,45 may be a thermal resistant material.

Figure 4:
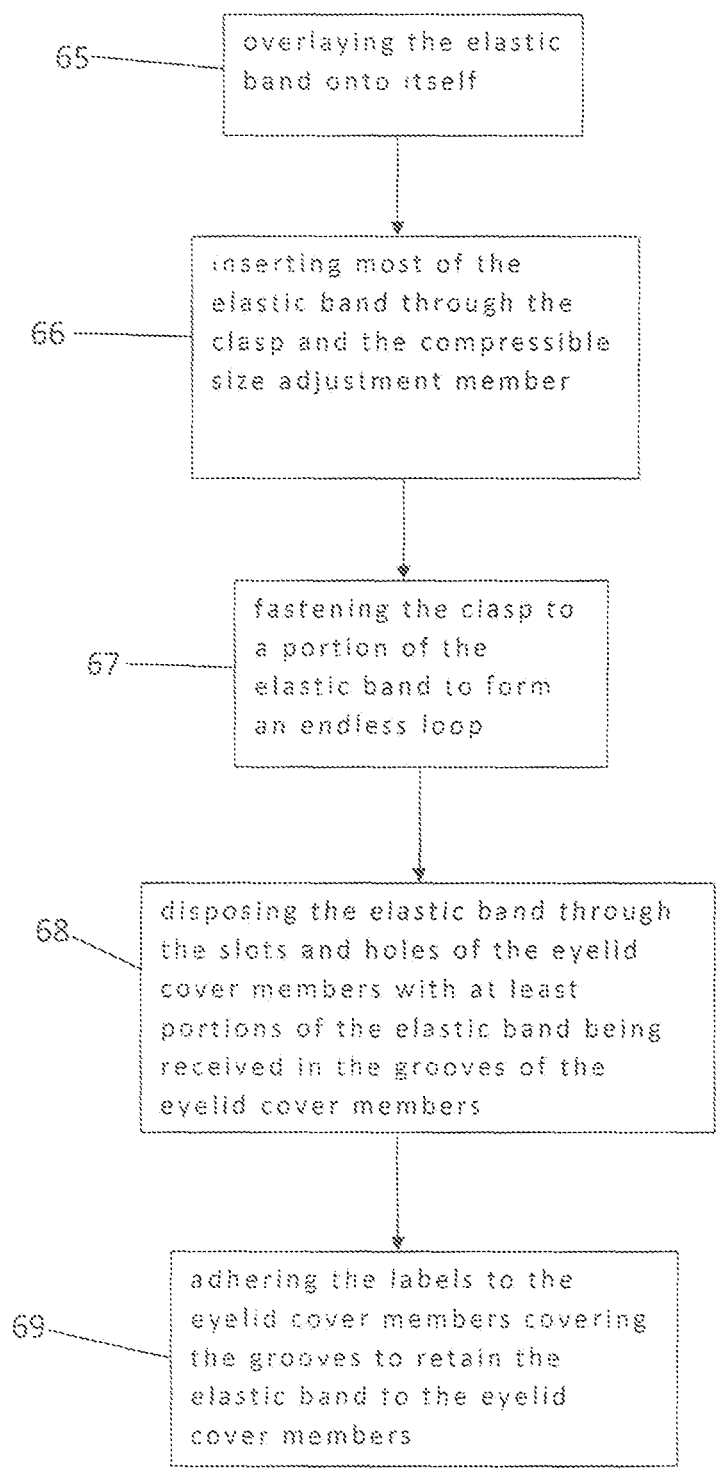
FIG. 4 is a flow diagram of the process of assembly the adjustable eyelid cover device.

As illustrated in FIG. 4, to assembly the eyelid cover device 10, the elastic band 38 may be strung and disposed through a hook of a needle and overlaid upon itself (block 65), and the needle with the pointed end opposite the hook may be inserted along with most of the elastic band 38 through the clasp 41 and the compressible size adjustment member 40 (block 66). Once most of the elastic band 38 is inserted through both the clasp 41 and the compressible size adjustment member 40, the clasp 41 may be fastened or crimped to a portion of the elastic band 38 not inserted through the compressible size adjustment member 40 to form an endless loop (block 67). Then the elastic band 38 may be inserted through the slots 50-53 and holes 17,18, 24,25 of the eyelid cover members 12,19 with at least portions of the elastic band 38 being received in the grooves 59,60 of the eyelid cover members 12,19 (block 68). To finish the assembling, the labels 26,32 may be adhered to the eyelid cover members 12,19 covering the grooves 59,60 to retain the elastic band 38 to the eyelid cover members 12,19 (block 69).

In use, the user removably secures the elastic band 38 about a user' head 46 and neck 54 region by sliding the elastic band 38 over the top of the user's head 46. The user then positions the eyelid cover members 12,19 about the user's head 46 and neck 54 region by spacing the eyelid cover members 12,19 upon the elastic band 38 and over the user's eyes and eyelids 48,49 as desired to properly fit over a user's eyelids 48,49 since the spacing of the eyes are unique and different for all users. When not using the eyelid cover members 12,19 to cover the user's eyelids 48,49, the user may place. the eyelid cover members 12,19 upon a user's forehead 47 with the indicia 31,37 being displayed outwardly from the user's forehead 47. As another embodiment, the user can fold the eyelid cover members 12,19 upon themselves and hang the elastic band 38 about the user's neck 54.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the adjustable eyelid cover device and method. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An adjustable eyelid cover device comprising:
   an eyelid cover assembly including a pair of eyelid cover members having a thickness being adapted to fit over a user's eyelids when a user has one's eyes closed, wherein each of the eyelid cover members is a thin, semi-flexible piece of material having a generally elliptical shape and having a pair of opposed through holes disposed there through and passing through the entire thickness of the respective eyelid cover member with each through hole disposed adjacent to a respective vertex of the piece of material, wherein each of the eyelid cover members also has a pair of slots each extending from the respective hole and disposed through an edge of the respective eyelid cover member at the respective vertex, wherein the eyelid cover assembly also includes a pair of labels each being a flexible piece of material and having an elliptical shape and also having dimensions substantially equivalent to that of the eyelid cover members;
   an elastic band or bands adjustably interconnecting the eyelid cover members and being adapted to fasten about a user's head to independently position the eyelid cover members over the user's eyelids; and
   a size adjustment member engagable to at least a portion of the elastic band or bands and adapted to adjust a size of the elastic band about the user's head;
   wherein the elastic band or bands extend through the opposed slots and through the opposed through holes of each of the eyelid cover members to interconnect the eyelid cover members and is also received in grooves on an outer surface of the eyelid cover members and is allowing the elastic cord to sit substantially flush with a convex outer surface of the eyelid cover member and is engagable to the labels to prevent the eyelid cover members from spinning upon the elastic band,
   wherein a clasp is fastened about end portions of the elastic band to form an endless loop;
   wherein the eyelid cover members are independently movably engaged upon the elastic band to be adjustable and accommodate all varying eye spacing's for all users.

2. The adjustable eyelid cover device as described in claim 1, wherein each of the labels has an inner surface which is adhered to the convex outer surface of the respective eyelid cover member, which retains the elastic cord in the groove of the eyelid covers.

3. The adjustable eyelid cover device as described in claim 2, wherein each of the labels also has an outer surface upon which selected indicia is displayed.

* * * * *